United States Patent [19]

Collins et al.

[11] 4,087,621

[45] May 2, 1978

[54] 7-{3-HYDROXY-2β-[4-HYDROXY-4-(LOWER ALKYL)-TRANS-1-OCTEN-1-YL]-5-OXOCYCLOPENT-1α-YL}HEPT-5-CIS-ENOIC ACIDS AND RELATED COMPOUNDS

[75] Inventors: Paul W. Collins, Deerfield; Raphael Pappo, Skokie, both of Ill.

[73] Assignee: G. D. Searle & Co., Chicago, Ill.

[21] Appl. No.: 630,394

[22] Filed: Nov. 10, 1975

Related U.S. Application Data

[63] Continuation-in-part of Ser. No. 454,913, Mar. 26, 1974, Pat. No. 3,965,143.

[30] Foreign Application Priority Data

Mar. 6, 1975 South Africa .................. 75/1391

[51] Int. Cl.$^2$ ........................................... C07C 177/00
[52] U.S. Cl. ........................ 560/231; 260/345.7 P; 260/345.8 P; 260/448.8 R; 260/514 D; 260/345.7 R; 260/345.8 R; 560/121
[58] Field of Search .......... 260/468 D, 514 D, 448 R, 260/448.8 R, 345.7, 345.8

[56] References Cited

FOREIGN PATENT DOCUMENTS 7,310,276   1/1974   Netherlands ..................... 260/468

*Primary Examiner*—Robert Gerstl
*Attorney, Agent, or Firm*—John J. McDonnell

[57] ABSTRACT

7-{3-Hydroxy-2β-[4-hydroxy-4-(lower alkyl)-trans-1-octen-1-yl]-5-oxocyclopent-1α-yl}hept-5-cis-enoic acids, displaying valuable pharmacological properties, e.g., gastric anti-secretory, are produced by the reaction of 7-(3-oxygenated-5-oxocyclopent-1-en-1-yl)hept-5-cis-enoic acid or ester with the appropriate organometallic reagent.

9 Claims, No Drawings

7-{3-HYDROXY-2β-[4-HYDROXY-4-(LOWER ALKYL)-TRANS-1-OCTEN-1-YL]-5-OXOCYCLOPENT-1α-YL}HEPT-5-CIS-ENOIC ACIDS AND RELATED COMPOUNDS

This application is a continuation-in-part of our copending application Ser. No. 454,913, filed March 26, 1974 now U.S. Pat. No. 3,965,143.

The present invention relates to novel 7-{3-hydroxy-2β-[4-hydroxy-4-(lower alkyl)-trans-1-octen-1-yl]-5-oxocyclopent-1α-yl}hept-5-cis-enoic acids and related compounds. More particularly, this invention provides new and useful compounds of the general formula

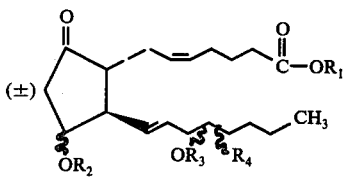

wherein $R_1$ is hydrogen or lower alkyl; $R_2$ is hydrogen or a lower alkanoyl, tetrahydropyran-2-yl, or tri(lower alkyl)-silyl radical; $R_3$ is hydrogen or a lower alkanoyl, lower alkyl, or tri(lower alkyl)silyl radical; $R_4$ is lower alkyl; and the wavy lines represent the alternative R or S configuration.

The lower alkyl radicals represented in the foregoing structural formula contain 1 to 7 carbon atoms and are typified by methyl, ethyl, propyl, butyl, pentyl, hexyl, heptyl, and the branched-chain radicals thereof.

The lower alkanoyl radicals denoted in the above formula are those containing 1 to 7 carbon atoms, i.e., formyl, acetyl, propionyl, butyryl, valeryl, caproyl, heptanoyl, and the branched-chain radicals corresponding.

The novel compounds of the present invention display valuable pharmacological properties as is exemplified by their ability to inhibit the gastric secretion stimulated by secretogogues such as histamine and pentagastrin while furthermore possessing the surprising advantage of lacking the potent undesirable side-effects displayed by related substances. In addition, these compounds are inhibitors of blood platelet aggregation and, moreover, display anti-fertility and bronchodilating properties.

The specific assay used to detect gastric antisecretory activity is described as follows:

Adult female beagle dogs weighing 13 – 20 kg. are prepared with denervated fundic Heidenhain pouches. After a recovery period of at least 4 weeks following surgery, the animals are fasted for approximately 20 hours, then are placed in Pavlov stands and infused intravenously with saline solution. The pouched secretions are collected every 15 minutes and measured for volume and total acidity by titration with 0.1N sodium hydroxide to pH 7.0. Following a 30 minute basal secretion the dogs are infused with a saline solution of histamine dihydrochloride at a dose of 1.0 mg./hr. The volume of the diffusion is kept at approximately 13 ml./hr. A steady state plateau of gastric secretion is obtained approximately 1 hour following the start of histamine infusion, at the end of which time the test compound dissolved in an ethanolic isoosmotic phosphate buffer solution is administered by a single intravenous injection. The duration of the anti-secretory effects is determined and the side-effects, if any, recorded. The compound is rated active if statistically significant inhibition of secretory parameters occur following compound treatment.

Starting materials suitable for use in the manufacture of the compounds of the present invention are the 7-(3-oxygenated-5-oxocyclopent-1-en-1-yl)hept-5-cis-enoic acids and esters of the following formula

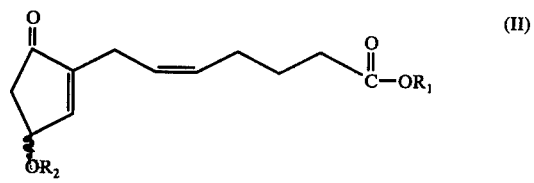

wherein $R_1$ and $R_2$ are as defined hereinbefore. Introduction of the oxygenated alkenyl side chain at the 2-position of the cyclopentane ring is effected by reaction with a suitable organometallic reagent. Particularly suitable reagents for introduction of the oxygenated alkenyl side chain are the alkenyl coppers and the lithium alkenyl cuprates prepared from the appropriate unsaturated alcohol. A convenient method for manufacture of the cuprate reagent comprises the reaction of an acetylenic alcohol of the following formula

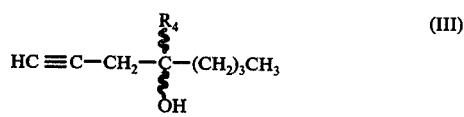

wherein $R_4$ and the wavy lines are as hereinbefore defined, with a trialkylsilyl halide to afford the corresponding trialkylsilyl ether, addition of catechol borane across the acetylenic bond to produce the boronic acid derivative, reaction of the latter substance with iodine to yield the 1-alkenyl iodide, which is contacted with a cuprous acetylide and a lithium alkyl to afford the desired lithium cuprate reagent. The latter processes are exemplified by the reaction of 4(RS)-4-methyl-1-octyn-4-ol with triethylsilyl chloride to afford 4(RS)-4-methyl-1-octyn-4-ol triethylsilyl ether, reaction of that ether with catechol borane to yield 4(RS)-4-methyl-4-triethylsilyloxy-trans-1-octenyl boronic acid, which is contacted with iodine to produce 4(RS)-4-methyl-4-triethylsilyloxy-trans-1-octenyl iodide. That halide is then allowed to react with n-butyl lithium and cuprous 1-pentynylide, thus affording racemic lithium[(1-pentynyl)-(4(RS)-4-methyl-4-triethylsilyloxy-trans-1-octenyl)cuprate].

Alternatively, the 4(RS)-4-methyl-4-triethylsilyloxy-trans-1-octenyl iodide may be prepared by contacting 4(RS)-4-methyl-1-octyn-4-ol triethylsilyl ether with a 20% diisobutyl aluminum hydride solution and treating the resultant product with iodine.

Reaction of the latter cuprate reagents with the aforementioned starting materials of formula (II), the manufacture of which compounds is detailed in Pappo and Jung U.S. Pat. No. 3,558,682, issued Jan. 26, 1971, and in Bruhn and Pappo German Offenlegungschrift No. 2,415,765 results in introduction of the oxygenated alkenyl side chain at the 2-position of the cyclopentane ring. As a specific example, methyl 7-(3(RS)-tetrahydropyran-2-yloxy-5-oxocyclopent-1-en-1-yl)hept-5-cis-enoate is allowed to react with lithium [(1-pentynyl)-(4(RS)-4-methyl-4-triethylsilyloxy-trans-1-octenyl)-cuprate], thus affording racemic methyl 7-[3(R)-tetrahydropyran-2-yloxy-2β-(4(RS)-4-methyl-4-triethylsilyloxy-trans-1-octen-1-yl)-5-oxocyclopent-1α-yl]hept-5-cis-enoate. Removal of the trialkylsilyl and tetrahydropyran-2-yl protecting groups is conveniently effected by reaction with acetic acid, thus producing a 1:1 mixture of racemic methyl 7-[3(R)-hydroxy-2β-(4(R)-4-hydroxy-4-methyl-trans-1-octen-1-yl)-5-oxocyclopent-1α-yl]-1α-hept-5-cis-enoate and racemic methyl 7-[3(R)-hydroxy-2β-(4(S)-4-hydroxy-4-methyl-trans-1-octen-1-yl)-5-oxocyclopent-1α-yl]hept-5-cis-enoate, which diastereoisomers are separable by high performance liquid chromatographic techniques.

Additional copper agents suitable for use in the manufacture of the instant compounds are the lithium divinyl cuprates and the vinyl coppers of the type described by Kluge et al., J. Amer. Chem. Soc., 94, 7827 (1972), the lithium vinyl cyano cuprates of the type described by Gorlier et al., Chem. Comm., 3, 88 (1973) and the lithium diorganocuprates as described by Mandeville et al., J. Org. Chem., 39, 400 (1974).

Reaction of the aforementioned 7-(3-oxygenated-5-oxocyclopent-1-en-1-yl)hept-5-cis-enoic acid and ester starting materials with an aluminum alkenyl organometallic reagent results in the instant compounds wherein the oxygenated function at the 3-position of the cyclopentane ring is in the epi stereochemical configuration. Typically, 4(RS)-4-methyl-1-octyn-4-ol is converted to the corresponding triethylsilyl ether by reaction with triethylsilyl chloride and that ether is contacted with diisobutylaluminum hydride to produce the aluminum alkenyl reagent. The latter reagent is allowed to react with methyl 7-(3(RS)-hydroxy-5-oxocyclopent-1-en-1-yl)-hept-5-cis-enoate, thus affording the racemic methyl 7-[(3(S)-hydroxy-2β-(4(RS)-4-methyl-4-triethylsilyloxy-trans-1-octen-1-yl)-5-oxocyclopent-1α-yl]hept-5-cis-enoates.

The mono and/or di-acylated derivatives of the present invention are conveniently produced by reaction of the corresponding hydroxy substances with a lower alkanoic acid anhydride or halide, preferably in the presence of a suitable acid acceptor such as pyridine or triethylamine. As a specific example, the aforementioned racemic methyl 7-[3(R)-hydroxy-2β-(4(S)-4-hydroxy-4-methyl-trans-1-octen-1-yl)-5-oxocyclopent-1α-yl]hept-5-cis-enoate is contacted with acetic anhydride and pyridine, thus affording racemic methyl 7-[3(R)-acetoxy-2β-(4(S)-4-acetoxy-4-methyl-trans-1-octen-1-yl)-5-oxocyclopent-1α-yl]hept-5-cis-enoate.

The optically active compounds of this invention may be produced by coupling of the optically active 7-(3-oxygenated-5-oxocyclopent-1-en-1-yl)hept-5-cis-enoates with the vinyl copper reagents derived from the acetylenic alcohols, and separating the resulting compounds by liquid chromatography. The 7-(3-oxygenated-5-oxocyclopent-1-en-1-yl)hept-5-cis-enoates are resolved by reaction with an optically active aminoxycarboxylic acid to afford the two diastereomeric oximes, which are separated chromatographically. Cleavage of the oxime moiety by treatment with titanium trichloride affords the individual 3(R) and 3(S) stereoisomers. Thus, for example, when methyl 7-[3(R)-hydroxy-5-oxocyclopent-1-en-1-yl]hept-5-cis-enoate and 4(RS)-4-methyl-1-octyn-4-ol are used as the starting materials in the processes described hereinbefore, methyl 7-[3(R)-hydroxy-2β-(4(RS)-4-hydroxy-4-methyl-trans-1-octen-1-yl)-5-oxocyclopent-1α-yl]-hept-5-cis-enoate is produced. This mixture is then separated by chromatographic methods to give the two isomers.

The invention will appear more fully from the examples which follow. It will be apparent to those skilled in the art that many modifications, both of materials and methods, may be practiced without departing from the purpose and intent of this disclosure. Throughout the examples hereinafter set forth, temperatures are given in degrees Centigrade (° C.) and relative amounts in parts by weight unless otherwise noted.

EXAMPLE 1

14.85 Parts of 5-chloropent-1-yne is dissolved in 250 parts by volume of toluene and the resulting solution is cooled to approximately −40° C. To that solution is then added 62.8 parts by volume of 2.31 M ethereal n-butyl lithium and stirring is continued for approximately 15 minutes. 6.87 Parts of boron trifluoride etherate is added and the reaction mixture is stirred for about two hours, then is allowed to stand for about 16 hours at −5° to −10° C. At the end of that time, 10.14 parts of methyl vinyl ketone is added at −40° C. and the reaction mixture is stirred for about 4 hours, then is quenched with water. 50 Parts by volume of 3 N hydrochloric acid is added and the mixture is kept at room temperature for about 16 hours, at the end of which time the aqueous and organic layers and separated. The aqueous layer is extracted with toluene and the organic layer with water. The organic solutions are combined, washed successively with aqueous sodium hydroxide and water, then dried over anhydrous sodium sulfate and stripped to dryness under reduced pressure to afford the crude product. This material is purified by distillation under reduced pressure to give 9-chloro-5-nonyn-2-one, boiling at about 80° − 92° C. at a pressure of 0.11 − 0.06 mm.

EXAMPLE 2

To a solution consisting of 2.77 parts of 9-chloro-5-nonyn-2-one in 8 parts by volume of ethanol is added a solution containing 2.77 parts of sodium cyanide dissolved in 4 parts of water. The resulting reaction mixture is heated at 80° − 100° C. for about 24 hours, then is cooled and diluted with ether, and then 20 parts by volume of dilute aqueous sodium hydroxide is added with stirring. The layers are separated and the alkaline layer is extracted with ether. The ether extracts are combined, washed with water, dried over anhydrous sodium sulfate, and concentrated under reduced pressure to afford 9-cyano-5-nonyn-2-one. This compound exhibits an infrared adsorption maximum at 2250 reciprocal centimeters and nuclear magnetic resonance peaks at $\delta 2.15$ and $\delta 2.50$.

EXAMPLE 3

A mixture consisting of 1.79 parts of 9-cyano-5-nonyn-2-one, 5 parts by volume of ethanol and 5 parts by volume of 5% aqueous sodium hydroxide is heated just below the reflux temperature for about 6 hours, then is cooled and extracted with chloroform. The alkaline layer is acidified with hydrochloric acid to pH 4, resulting in separation of a brown liquid. This material is extracted with chloroform and the chloroform solution is washed with water, dried over anhydrous sodium sulfate, and concentrated to dryness under reduced pressure to afford 9-oxo-5-decynoic acid. The compound exhibits nuclear magnetic resonance peaks at $\delta 2.18$, $\delta 2.50$, and $\delta 9.6$.

EXAMPLE 4

To a solution of 23.6 parts of 9-oxo-5-decynoic acid in a mixture of 999 parts by volume of benzene and 221.4 parts by volume of 1% quinoline in benzene is added 1.18 parts of 5% palladium-on-barium sulfate catalyst and the resulting mixture is shaken with hydrogen at atmospheric pressure and room temperature until 1 molecular equivalent of hydrogen is absorbed. The catalyst is removed by filtration and the filtrate is washed successively with dilute hydrochloric acid and water, dried over anhydrous sodium sulfate, and stripped of solvent under reduced pressure to produce 9-oxo-5-cis-decenoic acid, which exhibits nuclear magnetic resonance maxima at δ2.13 and δ5.39.

EXAMPLE 5

A solution of potassium tertiary-butoxide is prepared by dissolving 4.8 parts of potassium metal in 30 parts by volume of tertiary-butyl alcohol at reflux temperature under nitrogen. To that solution is then added a solution consisting of 3.7 parts of 9-oxo-5-cis-decenoic acid and 7.23 parts of dimethyl oxalate dissolved in 25 parts by volume of tertiary-butyl alcohol. The addition is conducted with stirring at the reflux temperature. After the reaction mixture is refluxed under nitrogen for about 2.5 hours, the colored supernatant is decanted. The remaining precipitate is dissolved in water, and acidified with dilute hydrochloric acid. Extraction of that acidic mixture with chloroform affords an organic solution, which is washed with saturated aqueous sodium chloride, dried over anhydrous sodium sulfate, and stripped of solvent under reduced pressure to afford 7-(2,3,5-trioxo-4-methoxalylcyclopent-1-yl)hept-5-cis-enoic acid, melting at about 99° – 104° C. and represented by the following structural formula.

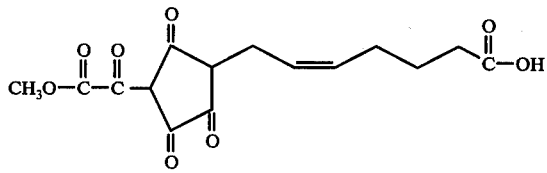

EXAMPLE 6

A mixture consisting of 10.6 parts of 7-(2,3,5-trioxo-4-methoxalylcyclopent-1-yl)hept-5-cis-enoic acid and 490 parts by volume of dilute hydrochloric acid is heated at the reflux temperature for about 3 hours, then is cooled and extracted with ethyl acetate. The organic extract is washed with saturated aqueous sodium chloride, dried over anhydrous sodium sulfate, and stripped of solvent under reduced pressure to afford the crude product. Purification of that material is effected by adsorption on a silicic acid chromatographic column followed by elution with ethyl acetate-benzene. From the eluate there is obtained pale yellow crystals of 7-(2,3,5-trioxocyclopent-1-yl)hept-5-cis-enoic acid, melting at about 84° – 85° C. and represented by the following structural formula.

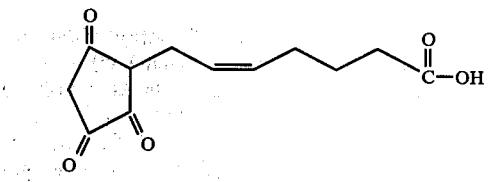

EXAMPLE 7

A solution of 0.54 part of 7-(2,3,5-trioxocyclopent-1-yl)hept-5-cis-enoic acid in 11 parts of water is neutralized by the addition of dilute aqueous sodium hydroxide. The neutralized solution is then cooled to 0° – 5° C., at which point 0.037 part of sodium borohydride is added. The reaction mixture is stirred at 0° – 5° C. for about 50 minutes, then is quenched by the addition of dilute hydrochloric acid to pH 1. The resulting solution is extracted several times with ethyl acetate. The ethyl acetate extracts are combined, washed with saturated aqueous sodium chloride, dried over anhydrous sodium sulfate, and concentrated to dryness under reduced pressure to afford white crystals of 7-(2,5-dioxo-3(RS)-hydroxycyclopent-1-yl)hept-5-cis-enoic acid, melting at about 83° – 85° C. This compound is represented by the following structural formula.

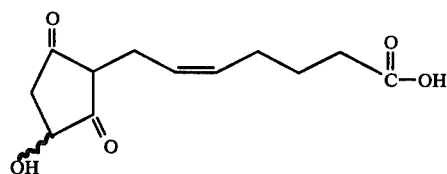

EXAMPLE 8

To a solution of 2.9 parts of 7-(2,5-dioxo-3(RS)-hydroxycyclopent-1-yl)hept-5-cis-enoic acid in 33.8 parts by volume of methanol, under nitrogen, is added, with stirring, 10.18 parts by volume of acetone dimethyl ketal followed by 3.97 parts by volume of 1.14% methanolic hydrogen chloride. The resulting reaction mixture is allowed to stand at room temperature for about 48 hours, then is stripped of solvent by distillation under reduced pressure. A small amount of ether is added and the mixture is allowed to stand for about 48 hours, then is dissolved in benzene containing 1% triethylamine. The resulting solution is washed successively with dilute aqueous potassium carbonate and water, then dried over anhydrous sodium sulfate and stripped of solvent under reduced pressure to afford white crystals of methyl 7-(4(RS)-hydroxy-2-methoxy-5-oxocyclopent-1-en-1-yl)hept-5-cis-enoate, melting at about 77° – 78° C. It exhibits nuclear magnetic resonance maxima at δ3.69, δ3.98, δ4.29 and δ5.39 and is represented by the following structural formula.

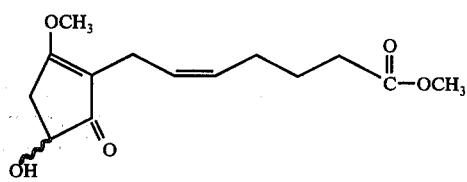

EXAMPLE 9

To a solution of 0.256 part of methyl 7-(4(RS)-hydroxy-2-methoxy-5-oxocyclopent-1-en-1-yl)hept-5-cis-enoate in a mixture consisting of 3.7 parts by volume of tetrahydrofuran and 4.4 parts by volume of toluene, under nitrogen, is added dropwise at −70° C., 0.33 part by volume of a 3.3 M sodium dihydro bis-(2-methoxyethoxy)aluminate in benzene solution. Stirring is continued at that temperature for about 5.5 hours, at the end of which time the reaction mixture is quenched by the addition of methanol. After an additional 10 minute stirring period, the mixture is allowed to warm to room temperature, then is acidified to pH 2 by the addition of dilute hydrochloric acid. The resulting two-phase mixture is extracted with ethyl acetate and the organic extract is washed with saturated aqueous sodium chloride, then dried over anhydrous sodium sulfate under reduced pressure to afford the crude product. That material is purified by adsorption on a silicic acid chromatographic column followed by elution with ethyl acetate in benzene to afford, as an oil, methyl 7-(3(RS)-hydroxy-5-oxocyclopent-1-en-1-yl)hept-5-cis-enoate. This compound exhibits nuclear magnetic resonance peaks at $\delta 3.68$, $\delta 5.55$, and $\delta 7.20$, and is represented by the following structural formula.

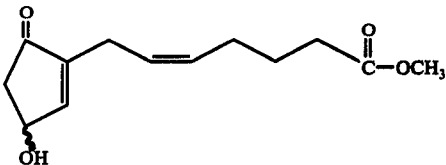

EXAMPLE 10

To a solution of 1.74 parts of methyl 7-(3(RS)-hydroxy-5-oxocyclopent-1-en-1-yl)hept-5-cis-enoate in 12 parts by volume of dry benzene is added 0.005 part of p-toluenesulfonic acid and 1.74 parts of dihydropyran. The reaction mixture is stirred for 5 minutes under a nitrogen atmosphere and then allowed to stand at room temperature for a further 2 hours. The resulting solution is diluted with ethyl acetate, washed with water, dried over anhydrous sodium sulfate, and stripped of solvent under reduced pressure to afford methyl 7-(3(RS)-tetrahydropyran-2-yloxy-5-oxocyclopent-1-en-1-yl)hept-5-cis-enoate.

EXAMPLE 11

A mixture consisting of 2.8 parts of 4(RS)-4-methyl-1-octyn-4-ol, 3.5 parts of triethylsilyl chloride, 10 parts by volume of dimethylformamide and 3 parts by volume of triethylamine is heated at the reflux temperature for about 16 hours, then is cooled and diluted with ether. That organic solution is then washed successively with dilute hydrochloric acid and water, dried over anhydrous sodium sulfate and stripped of solvent under reduced pressure. Adsorption of the residue on a silica gel chromatographic column followed by elution with hexane affords 4(RS)-4-methyl-1-octyn-4-ol triethylsilyl ether, characterized by a nuclear magnetic resonance maximum at $\delta 2.3$.

To a solution of 1.27 parts of 4(RS)-methyl-1-octyn-4-ol triethylsilyl ether in 10 parts by volume of hexane is added, in a nitrogen atmosphere, at about 0° C, 4 parts of a 20% diisobutyl aluminum hydride solution in toluene. The resulting reaction mixture is allowed to stand at room temperature for about 16 hours, then is warmed at about 60° C. for 2 hours. After cooling, the solution is partially concentrated, then diluted with approximately 5 parts by volume of tetrahydrofuran and cooled to about 0° C. To that mixture is then added dropwise a solution consisting of 1.25 parts of iodine dissolved in 5 parts by volume of tetrahydrofuran. After the addition is complete, the mixture is partitioned between ether and hydrochloric acid. The ether layer is separated, washed successively with dilute aqueous sodium sulfite and water, then dried over anhydrous sodium sulfate and stripped of solvent under reduced pressure. The resulting residue is purified by chromatography on a silica gel column followed by elution with hexane, thus affording 4(RS)-4-methyl-4-triethylsilyloxy-trans-1-octenyl iodide. This compound is characterized by nuclear magnetic resonance spectrum peaks at about $\delta 1.15$ and $\delta 5.95$.

EXAMPLE 12

A mixture consisting of 2.55 parts of 4(RS)-4-methyl-1-octyn-4-ol triethylsilyl ether and 1.3 parts of catechol borane is warmed at 60° - 70° C. for about 5 hours, then cooled and poured into cold water. The resulting aqueous mixture is stirred vigorously for about 15 minutes, then extracted with ether. The ether layer is separated, then washed several times with dilute aqueous potassium hydroxide and stripped of solvent under reduced pressure. The resulting residue is extracted with hexane and the hexane extract is washed twice with a solution consisting of 35 parts of potassium hydroxide dissolved in 25 parts of water and 100 parts by volume of methanol. Those alkaline extracts are combined, cooled to 0° - 5° C., then carefully acidified by the addition of dilute hydrochloric acid. That acidic solution is extracted with ether and the ether extract is washed with water, dried over anhydrous sodium sulfate and stripped of solvent by distillation under reduced pressure, thus affording, as a brown viscous oil, 4(RS)-4-methyl-4-triethylsilyloxy-trans-1-octenyl boronic acid.

To a solution of 1.23 parts of 4(RS)-4-methyl-4-triethylsilyloxy-trans-1-octenyl boronic acid dissolved in 10 parts of methanol is added, at 0° C., a solution consisting of 0.32 part of sodium hydroxide dissolved in 3 parts of water. To that cold mixture is then added dropwise a solution of 1.01 parts of iodine dissolved in 20 parts by volume of methanol. After the addition is complete, the mixture is diluted with ether, washed with water and dried over anhydrous sodium sulfate. Removal of the solvent by distillation under reduced pressure affords 4(RS)-4-methyl-4-triethylsilyloxy-trans-1-octenyl iodide, identical to the product of Example 11.

EXAMPLE 13

Substitution of an equivalent quantity of 4(RS)-4-ethyl-1-octyn-4-ol [prepared according to the method of Nobubara, Agr. Biol. Chem., 32(8), p. 1016 (1968)] for the 4(RS)-4-methyl-1-octyn-4-ol used in Example 11, and substantial repetition of the procedure detailed therein affords 4(RS)-4-ethyl-4-triethylsilyl-trans-1-octenyl iodide.

EXAMPLE 14

To a solution of 5.58 parts of 4(RS)-4-methyl-4-triethylsilyloxy-trans-1-octenyl iodide in 38 parts by volume ether, under a nitrogen atmosphere, is added, at −65° C., 5.70 parts by volume of a 2.56 M n-butyl lithium solution in hexane. The resulting mixture is stirred for about 30 minutes, at the end of which time a solution consisting of 6.66 parts of copper 1-pentynilide bis-hexamethylphosphorus triamide (prepared from copper 1-pentynilide and hexamethylphosphorus triamide) dissolved in 38 parts by volume of ether is added with stirring. Stirring is continued for an additional 20 minutes, at the end of which time a solution consisting of 2.35 parts of methyl 7-(3(RS)-tetrahydropyran-2-yloxy-5-oxocyclopent-1-en-1-yl)hept-5-cis-enoate dissolved in 19 parts by volume of ether is added dropwise. The resulting mixture is stirred at about −63° to −66° C. for approximately 2.5 hours. The reaction mixture is then partitioned between ether and cold dilute hydrochloric acid. The ether layer is separated, diluted with approximately 500 parts by volume of an ether-ethyl acetate mixture, washed once with water, filtered, dried over anhydrous sodium sulfate, and stripped of solvent by distillation under reduced pressure. The resulting residue is purified by chromatography on a silica gel column, using a 30:70 mixture of ethyl acetate and benzene as the eluant. Removal of the solvent from the eluant affords racemic methyl 7-[(3(R)-tetrahydropyran-2-yloxy)-2β-(4(RS)-4-hydroxy-4-triethylsilyloxy-trans-1-octen-1-yl)-5-oxocyclopent-1α-yl]hept-5-cis-enoate.

A solution consisting of 0.85 part of the latter compound dissolved in 50 parts by volume of a 3:1:1 acetic acid:water:tetrahydrofuran mixture is allowed to stand at room temperature for about 16 hours, then is diluted with a 1:1 benzene-ether mixture. The resulting ether-benzene solution is washed several times with water, dried over anhydrous sodium sulfate, stripped of solvent under reduced pressure and purified by chromatography using 100% ethyl acetate as eluant. Removal of the solvent from the eluant affords racemic methyl 7-[3(R)-hydroxy-2β-(4(RS)-4-hydroxy-4-methyl-trans-1-octen-1-yl)-5-oxocyclopent-1α-yl]hept-5-cis-enoate. This compound is characterized by nuclear magnetic resonance spectrum peaks at δ1.19, δ1.68, δ2.75, and δ4.09 and is represented by the following structural formula.

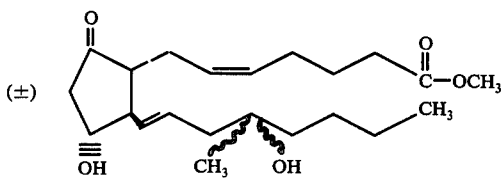

EXAMPLE 15

142 Parts of methyl 7-[3(RS)-hydroxy-5-oxocyclopent-1-en-1-yl]hept-5-cis-enoate was dissolved in 2.2 parts of methanol and 0.27 part of pyridine. To the mixture was added 119 parts of 2(R)-aminoxyisocaproic acid, heat, and the mixture was stirred for about 5 minutes then was allowed to stand at room temperature for 24 hours. The solvent was removed under reduced pressure, and the residue which remained was taken up in ethyl acetate, washed with dilute hydrochloric acid, then washed with water, dried over anhydrous sodium sulfate and stripped of solvent. The residue was extracted with ethyl acetate and then eluted on a silica column using 0.5% acetic acid/1.25% 2-propanol in methylene chloride as eluant to afford pure methyl 7-{3(R)-hydroxy-5-[(1-carboxyisoamyl)oxyimino]cyclopent-1-en-1-yl}hept-5-cis-enoate represented by the following structural formula

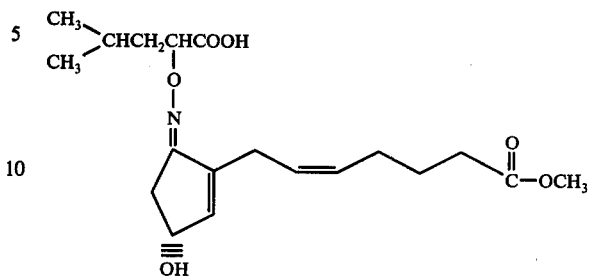

and pure methyl 7-{3(S)-hydroxy-5-[(1-carboxyisoamyl)oxyimino]-cyclopent-1-en-1-yl}hept-5-cis-enoate represented by the following structural formula.

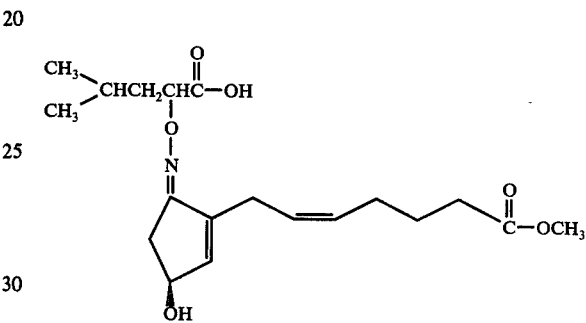

0.22 Part of the above (R)-hydroxy-5-oxime compound was dissolved in 9.8 parts of redistilled tetrahydrofuran and then treated with 1.7 parts of ammonium acetate in 17 parts of water to give a two phase system. To the mixture was added 1 part by volume of a 20% aqueous solution of titanium chloride and the mixture was stirred under nitrogen at 60° C. for about 1 hour. The solvents were removed under reduced pressure. The concentrated solution was then diluted with ethyl acetatebenzene, extracted with ethyl acetate-ether, washed with dilute hydrochloric acid, washed with water and dried over anhydrous sodium sulfate and stripped of solvent to yield methyl 7-[3(R)-hydroxy-5-oxocyclopent-1-en-1-yl]hept-5-cis-enoate, which exhibits a specific rotation, at 20° C. at a concentration of 0.95% of +8.4° in methanol.

When the procedure detailed in the last paragraph was repeated using the corresponding 3(S)-hydroxy-5-oxime compound, there was obtained methyl 7-[3(S)-hydroxy-5-oxocyclopent-1-en-1-yl]hept-5-cis-enoate, which exhibits a specific rotation, at 20° C., at a concentration of 0.95% of −9.9° in methanol.

EXAMPLE 16

When an equivalent quantity of methyl 7-(3(R)-hydroxy-5-oxocyclopent-1-en-1-yl)hept-5-cis-enoate is substituted for the methyl 7-(3(RS)-hydroxy-5-oxocyclopent-1-en-1-yl)hept-5-cis-enoate used in Example 10, and the procedures of Examples 10 and 14 substantially repeated, there are obtained after separation by liquid chromatography methyl 7-[(3(RS)-hydroxy-2β-(4(R)-4-hydroxy-4-methyl-trans-1-octen-1-yl)-5-oxocyclopent-1α-yl]hept-5-cis-enoate represented by the following structural formula

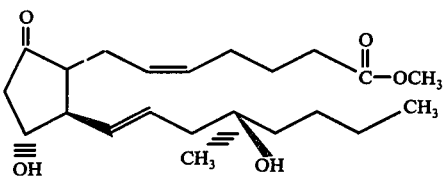

and methyl 7-[(3(R)-hydroxy-2β-(4(S)-4-hydroxy-4-methyl-trans-1-octen-1-yl-5-oxocyclopent-1α-yl]hept-5-cis-enoate, represented by the following structural formula.

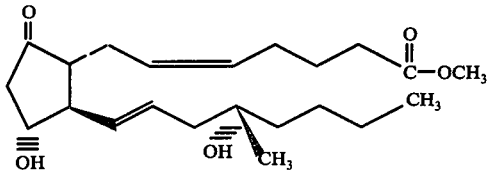

EXAMPLE 17

When an equivalent quantity of 4(RS)-4-ethyl-4-triethylsilyl-trans-1-octenyl iodide is substituted for the 4(RS)-4-methyl-4-triethylsilyloxy-trans-1-octenyl iodide used in Example 14, and the procedure detailed therein is substantially repeated, there is obtained racemic methyl 7-[3(R)-hydroxy-2β-(4(RS)-4-ethyl-4-hydroxy-trans-1-octen-1-yl)-5-oxocyclopent-1α-yl]hept-5-cis-enoate. This compound is represented by the following structural formula.

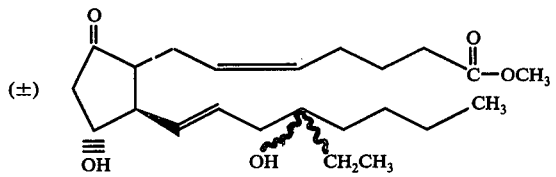

EXAMPLE 18

A mixture consisting of 25 parts of methyl 7-[3(R)-hydroxy-2β-(4(S)-4-hydroxy-4-methyl-trans-1-octen-1-yl)-5-oxocyclopent-1α-yl]hept-5-cis-enoate, 10 parts of acetic anhydride and 10 parts of pyridine is allowed to stand at room temperature for about 16 hours, then is poured carefully into cold excess aqueous citric acid. The resulting aqueous mixture is allowed to stand at room temperature for about 1 hour, then is extracted several times with ether. The combined ether extracts are washed with cold water, dried over anhydrous sodium sulfate and concentrated under reduced pressure. The resulting residue is purified by adsorption on a silicic acid chromatographic column followed by elution with ethyl acetate in benzene, thus affording methyl 7-[3(R)-acetoxy-2β-(4(S)-4-acetoxy-4-methyl-trans-1-octen-1-yl)-5-oxocyclopent-1α-yl]hept-5-cis-enoate. This compound is represented by the following structural formula.

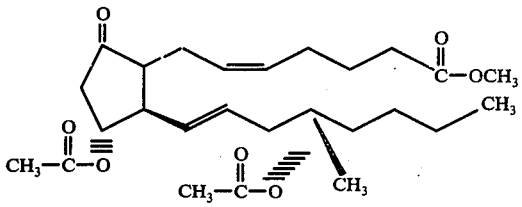

EXAMPLE 19

To a solution of 2 parts of 4(RS)-4-methyl-1-octyn-4-ol triethylsilyl ether in approximately 10 parts by volume of hexane is added, at −30° C., 7 parts of a 20% diisobutylaluminum hydride in toluene solution and the resulting reaction mixture is allowed to stand at room temperature for about 16 hours. It is then warmed at about 60° C. for 2 hours, cooled to about −60° C., and a solution of 0.96 part of methyl 7-(3(RS)-hydroxy-5-oxocyclopent-1-en-1-yl)hept-5-cis-enoate in 10 parts by volume of ether is added. Stirring at about −60° C. is then continued for 3 hours. The reaction mixture is then partitioned between ether and 1N hydrochloric acid, and the ether layer is separated, washed with water, dried over anhydrous sodium sulfate and stripped of solvent under reduced pressure. Chromatography on a silica gel column followed by elution with a 10:90 ethyl acetate-benzene mixture affords racemic methyl 7-[3(S)-hydroxy-2β-(4(RS)-4-methyl-4-triethylsilyloxy-trans-1-octen-1-yl)-5-oxocyclopent-1α-yl]hept-5-cis-enoate.

The latter product is dissolved in a 3:1:1 acetic acid:water:tetrahydrofuran solution and kept at room temperature for about 16 hours, following which period of time the reaction mixture is extracted with ether. The ether layer is washed several times with water, dried over anhydrous sodium sulfate and stripped of solvent under reduced pressure. The residue is then chromatographed on a silica gel column to afford racemic methyl 7-[3(S)-hydroxy-2β-(4(RS)-4-hydroxy-4-methyl-trans-1-octen-1-yl)-5-oxocyclopent-1α-yl]hept-5-cis-enoate, represented by the following structural formula.

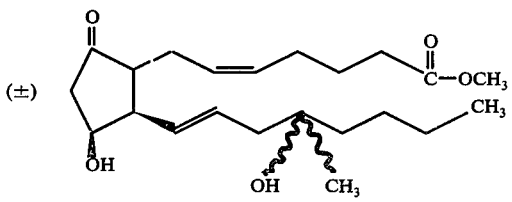

EXAMPLE 20

To a solution of 0.238 part of methyl 7-(3(RS)-hydroxy-5-oxocyclopent-1-en-1-yl)hept-5-cis-enoate in 4 parts by volume of methanol is added a solution consisting of 0.04 parts of sodium hydroxide in 1 part of water and the resulting reaction mixture is allowed to stand, in an atmosphere of nitrogen, at 0° − 5° C. for about 16 hours. At the end of that time the reaction mixture is acidified by the addition of 1.1 part by volume of 1 N hydrochloric acid, then is concentrated to a small volume at room temperature under reduced pressure. Extraction of that acidic mixture with ethyl acetate affords an organic solution, which is washed with aqueous sodium chloride, dried over anhydrous sodium sulfate and evaporated to dryness under reduced pressure, thus affording the crude product. Purification of that substance is effected by adsorption on a silicic acid chromatographic column followed by elution with ethyl acetate in benzene, thus affording 7-(3(RS)-hydroxy-5-oxocyclopent-1-en-1-yl)hept-5-cis-enoic acid.

EXAMPLE 21

When the resolved free acids of the compounds prepared in Example 15 are desired, the procedure of Example 15, first paragraph, is repeated to yield the resolved 3(R)- and 3(S)- hydroxy oxime esters. The resolved, separated oxime esters are then hydrolyzed according to the procedure detailed in Example 20 to yield pure 7-{33(R)-hydroxy-5-[(1-carboxyisoamyl)oxyimino]cyclopent-1-en-1-yl}hept-5-cis-enoic acid and pure 7-{3(S)-hydroxy-5-[(1-carboxyisoamyl)oxyimino]cyclopent-1-en-1-yl}hept-5-cis-enoic acid.

The resolved 3(R)- and 3(S)- hydroxy oxime acids are then treated in the manner described in the second and third paragraphs of Example 15 to afford 7-[3(R)-hydroxy-5-oxocyclopent-1-en-1-yl]hept-5-cis-enoic acid and 7-[3(S)-hydroxy-5-oxocyclopent-1-en-1-yl]hept-5-cis-enoic acid.

EXAMPLE 22

To a solution of 1.70 parts of 7-(3(R)-hydroxy-5-oxocyclopent-1-en-1-yl)hept-5-cis-enoic acid in 12 parts by volume of dry benzene is added 0.005 part of p-toluenesulfonic acid and 3.40 parts of dihydropyran. The reaction mixture is allowed to stand at room temperature for about 24 hours. The resulting solution is diluted with ethyl acetate, washed with water, dried over anhydrous sodium sulfate, and stripped of solvent under reduced pressure to afford tetrahydropyran-2-yl 7-(3(R)-tetrahydropyran-2-yloxy-5-oxocyclopent-1-en-1-yl)hept-5-cis-enoate. This compound is represented by the following structural formula.

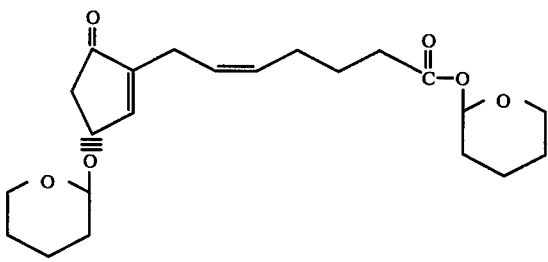

EXAMPLE 23

A solution of 1.85 parts of 4(RS)-4-methyl-4-triethylsilyloxy-trans-1-octenyl iodide in 10 parts by volume of ether is cooled to about −60° C. and 2.33 parts by volume of a 2.14 M n-butyl lithium in hexane solution is added. That mixture is stirred for about 30 minutes, at the end of which time a solution of copper 1-pentynylide bis-hexamethylphosphorus triamide (prepared from 0.65 part of pentynyl copper and 1.63 parts of hexamethylphosphorus triamide) in 5 parts by volume of ether is added. The resulting mixture is stirred at −60° C. for 10 minutes and a solution of 0.75 part of tetrahydropyran-2-yl 7-(3(R)-tetrahydropyran-2-yloxy-5-oxocyclopent-1-en-1-yl)hept-5-cis-enoate in 3 parts by volume of ether is added. That mixture is stirred first at −60° C. for 1 hour, then at −20° C. for an additional hour, then is diluted with ether. The ether solution is washed successively with dilute hydrochloric acid and water, then concentrated to dryness under reduced pressure. The residue is extracted with a 3:1:1 mixture of acetic acid:tetrahydrofuran:water and the extract is allowed to stand at room temperature for about 16 hours, then is diluted with ether and extracted with 5% aqueous potassium carbonate. The alkaline extract is washed with ether, acidified with dilute hydrochloric acid and extracted with ether. The resulting ether solution is washed with water, dried over anhydrous sodium sulfate and stripped of solvent under reduced pressure to afford after chromatography 7-[(3(R)-hydroxy-2β-(4(R)-4-hydroxy-4-methyl-trans-1-octen-1-yl)-5-oxocyclopent-1α-yl]hept-5-cis-enoic acid represented by the following structural formula

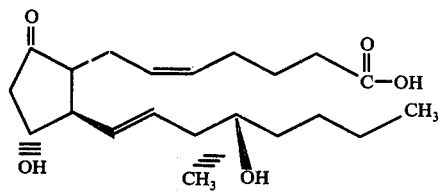

and 7-[3(R)-hydroxy-2β-(4(S)-4-hydroxy-4-methyl-trans-1-octen-1-yl)-5-oxocyclopent-1α-yl]hept-5-cis-enoic acid represented by the following structural formula.

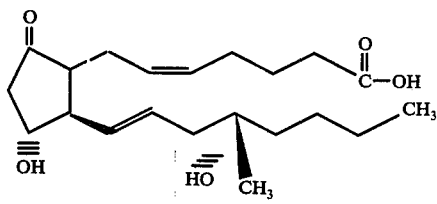

What is claimed is:

1. A compound of the formula

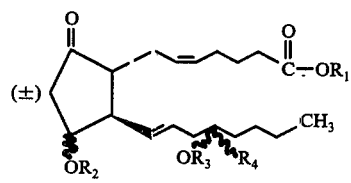

wherein $R_1$ is hydrogen or lower alkyl; $R_2$ is hydrogen or a lower alkanoyl, tetrahydropyran-2-yl, or tri(lower alkyl)silyl radical; $R_3$ is hydrogen or a lower alkanoyl, or tri(lower alkyl)-silyl radical; $R_4$ is a lower alkyl radical; and the wavy lines represent the alternative R or S configuration.

2. The compound according to claim 1 which is 7-[(3(R)-hydroxy-2β-(4(R)-4-hydroxy-4-methyl-trans-1-octen-1-yl)-5-oxocyclopent-1α-yl]hept-5-cis-enoic acid.

3. The compound according to claim 1 which is racemic 7-[(3(R)-hydroxy-2β-(4(S)-4-hydroxy-4-methyl-trans-1-octen-1-yl)-5-oxocyclopent-1α-yl]hept-5-cis-enoic acid.

4. The compound according to claim 1 which is racemic methyl 7-[3(S)-hydroxy-2β-(4(RS)-4-hydroxy-4-methyl-trans-1-octen-1-yl)-5-oxocyclopent-1α-yl]hept-5-cis-enoate.

5. The compound according to claim 1 of the formula

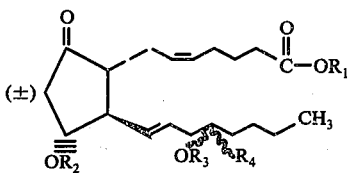

wherein $R_1$ is hydrogen or lower alkyl; $R_2$ is hydrogen or a lower alkanoyl or tetrahydropyran-2-yl radical; $R_3$ is hydrogen or a lower alkanoyl radical; $R_4$ is lower alkyl; and the wavy lines represent the alternative R or S configuration.

6. The compound according to claim 1 which is racemic methyl [3(R)-acetoxy-2β-(4(S)-4-acetoxy-4-methyl-trans-1-octen-1-yl)-5-oxocyclopent-1α-yl]hept-5-cis-enoate.

7. The compound according to claim 1 which is methyl 7-[(3(R)-hydroxy-2β-(4(R)-4-hydroxy-4-methyl-trans-1-octen-1-yl-5-oxocyclopent-1α-yl]hept-5-cis-enoate.

8. The compound according to claim 1 which is methyl 7-[(3(R)-hydroxy-2β-(4(S)-4-hydroxy-4-methyl-trans-1-octen-1-yl)-5-oxocyclopent-1α-yl]hept-5-cis-enoate.

9. The compound according to claim 1 which is racemic methyl 7-[3(R)-hydroxy-2β-(4(RS)-4-ethyl-4-hydroxy-trans-1-octen-1-yl)-5-oxocyclopent-1α-yl]hept-5-cis-enoate.

* * * * *